United States Patent [19]

Miyata et al.

[11] Patent Number: 5,837,735
[45] Date of Patent: Nov. 17, 1998

[54] ANTIINFLAMMATORY AGENT FOR EXTERNAL USE

[75] Inventors: Satoru Miyata; Yasuaki Taniguchi; Kenji Masuda; Yoichi Kawamura, all of Tosu, Japan

[73] Assignee: Helsinn Healthcare S.A., Pazzallo, Switzerland

[21] Appl. No.: 809,936

[22] PCT Filed: Oct. 5, 1995

[86] PCT No.: PCT/JP95/02045

§ 371 Date: Jul. 10, 1997

§ 102(e) Date: Jul. 10, 1997

[87] PCT Pub. No.: WO96/11002

PCT Pub. Date: Apr. 18, 1996

[30] Foreign Application Priority Data

Oct. 5, 1994 [JP] Japan .................................. 6-268293

[51] Int. Cl.⁶ ..................................................... A61K 31/18

[52] U.S. Cl. ............................. 514/605; 514/887; 514/969
[58] Field of Search ...................................... 514/605, 887, 514/969

[56] References Cited

U.S. PATENT DOCUMENTS 3,840,597  10/1974  Moore et al. ......................... 260/556 F

FOREIGN PATENT DOCUMENTS 55139313   of 1980   Japan .
01025719 A2 of 1989   Japan .
WO 8600014
       A2  of 1986   WIPO .

*Primary Examiner*—Leonard Schenkman
*Attorney, Agent, or Firm*—Young & Thompson

[57] ABSTRACT

An antiinflammatory agent for external use, containing nimesulide as the active ingredient dispersed in the base component and being well absorbable, safe and discoloration-free.

8 Claims, No Drawings

ANTIINFLAMMATORY AGENT FOR EXTERNAL USE

FIELD OF THE INDUSTRIAL USE

The present invention relates to an antiinflammatory agent for external use comprising nimesulide as an active ingredient. In particular, the present invention relates to an antiinflammatory agent for external use comprising nimesulide as an active ingredient and a base component wherein the nimesulide is mixed in a dispersed state in the base component, as well as to a process for preparing the same.

PRIOR ART

Non-steroidal antiinflammatory preparations have a disadvantage that, when orally administered, they cause gastrointestinal tract disorders. In order to avoid this disadvantage, various studies have been made to develop antiinflammatory agent for external use and several commercial products have been provided for clinical use. However, the antiinflammatory agent for external use hitherto developed have insufficient clinical effects even if they show effects in the basic tests.

Nimesulide (4-nitro-2-phenoxymethanesulfonanilide), which is one of the non-steroidal antiinflammatory agents, was first synthesized by Riker Co. in the United States and then developed as an oral preparation in Europe by Helsinn Co. in Switzerland. Being different from the conventional acidic antiinflammatory agents, it is known that nimesulide selectively inhibits PGE2 (COX2) and this is a new type of pharmaceutical agent expected to take effects in clinical use.

As the prior art regarding nimesulide, the substance patent described in U.S. Pat. No. 3,840,597 and process patents described in the examined Japanese patent publication (Kokoku) Sho-58-35989, the examined Japanese patent publication (Kokoku) Sho-58-50984 and the examined Japanese patent publication (Kokoku) Sho-59-44311 may be cited. However, these prior art references do not have descriptions or working examples regarding the actual pharmaceutical preparations, although they mention dosage forms such as capsule, cream, gel, tape, and the like.

In addition, the laid-open Japanese patent application (Kohyo) Hei-6-502842 based on the international patent application may be cited as a reference relating to the pharmaceutical preparation of nimesulide. This patent is to prepare an inclusion compound of nimesulide with cyclodextrin to make nimesulide water-soluble so as to increase water-solubility and to increase absorption of nimesulide in the gastrointestinal tract. Therefore, its object is not the external use. Thus, no reference is known which illustratively discloses use of nimesulide as an external preparation, and no case is known with respect to the actual external use of nimesulide in a particular dosage form.

It would be due to the fact that, although nimesulide has pharmacological effects equal to or higher than those of indomethacin which is regarded as a potent antiinflammatory agent, it has several unsolved problems when topically applied as an external preparation. That is, (1) nimesulide is hardly soluble and is not easily dissolved in water and various organic solvents. (2) A solvent which has strong solubilizing ability should be mixed to dissolve nimesulide, causing problems such as skin irritation, chapped skin, itch, and flare. (3) Even if nimesulide is dissolved, the resulting pharmaceutical preparation becomes deep yellow and thus its appearance becomes bad. (4) The pharmaceutical preparation applied soils clothes that contact the preparation.

Thus, there is a situation that the attempt to use nimesulide as the external preparation was abandoned.

Problems to be Solved by the Invention

The object of the present invention is to obtain an antiinflammatory agent for external use including nimesulide for topical use, which is a nimesulide external preparation showing excellent absorption and having no problem in coloring and skin safety.

Means for Solving the Problems

As a result of extensive studies taking the above-described disadvantages of nimesulide as an external preparation into consideration, the present inventors found that the above-described disadvantages are all solved when nimesulide is mixed in a dispersed state in a base component, and completed the present invention. That is, when nimesulide is mixed in a dispersed state in a base component, it surprisingly shows pharmacological effects equal to or higher than those of the pharmaceutical preparation in which nimesulide is mixed in a dissolved form. In addition, the amount of a solubilizing agent can be reduced and therefore the skin safety is improved. Furthermore, it is proved that the coloring of the pharmaceutical preparation does not occur, which is different from the completely dissolved-type pharmaceutical preparation. That is, all the above-described problems as the external preparation can be solved.

In particular, the object of the present invention is achieved by mixing nimesulide as an active ingredient in a dispersed state in a base component which comprises an oily substance, a nonionic surface active agent, a basic substance, water and/or an absorption enhancer. More particularly, 0.1 to 5% by weight of nimesulide as an active ingredient in a form of fine particles is dispersed and mixed in the base component which further comprises a hydrophilic polymer or a white petrolatum to prepare an external preparation such as cream or ointment.

Nimesulide as an active ingredient may be used in any form as long as it can be made into a dispersed state in a base component. In view of the easiness in grinding of the particles to be dispersed and the cost, the mean particle diameter of nimesulide is preferably 0.01 $\mu$m or more. On the other hand, in view of the transdermal absorbability and feeling on application (rough feeling), it is preferably 75 $\mu$m or less, i.e., the particle sizes that pass through a 200-mesh sieve, and more preferably from 0.5 to 50 $\mu$m, and further preferably from 1 to 30 $\mu$m.

The antiinflammatory agent for external use of the present invention may be prepared as follows. For example, the cream agent is prepared by mixing and stirring an oil phase of heat-melted oil components and an aqueous phase in which water-soluble components have been dissolved; adding nimesulide in a form of fine particles; and further carrying out stirring and cooling. The ointment is prepared by adding nimesulide in a form of fine particles into the heat-melted oil components with stirring and cooling, and further carrying out stirring and cooling.

The pH of the pharmaceutical preparation may desirably be controlled from 4 to 8, more preferably from 5 to 7, in view of the skin irritation and the transdermal absorbability.

Examples of the base to prepare the antiinflammatory agent for external use of the present invention include a so-called gel cream comprising a hydrophilic polymer, an oily substance, a nonionic surface active agent, a basic substance, and water; a vanishing cream produced from a higher alcohol, a hydrocarbon, a fatty acid ester, a polyhydric alcohol, a base, an antiseptic, water, and the like; a hydrophilic ointment or an absorptive ointment cream according to *The Japanese Pharmacopeia* produced from a white petrolatum, a surface active agent, a higher alcohol, a hydrocarbon, a fatty acid ester, a polyhydric alcohol, an antiseptic, water, and the like; and the FAPG base comprising a higher alcohol, polyhydric alcohol, and the like. As the prescription for the cream agent, a pharmaceutical preparation obtained by mixing 0.1 to 5% by weight of nimesulide in a so-called gel cream base comprising 0.2 to 3% by weight of a hydrophilic polymer, 2 to 20% by weight of an oily substance, 0.5 to 7% by weight of a nonionic surface active agent, 0.01 to 5% by weight of a basic substance, and 50 to 90% by weight of water is the most preferable from the viewpoint of the transdermal absorption. As the prescription for the ointment preparation, a pharmaceutical preparation obtained by mixing 0.1 to 5% by weight of nimesulide in a petrolatum ointment comprising 35 to 80% by weight of a white petrolatum, 2 to 20% by weight of an oily substance, and 0.5 to 7% by weight of a nonionic surface active agent is the most preferable.

Then, the base components of the present invention are described in further detail.

Examples of the hydrophilic polymer include carboxyvinyl polymers (CARBOPOL 940, 941 manufactured by B. F. Goodrich Chemical Co., HIBISWAKO 104, 105, manufactured by Wako Pure Chemical Industries, Ltd., and the like), hydroxypropylcellulose (HPC-L, HPC-M manufactured by Nippon Soda Co., Ltd., and the like), polyoxyethylenepolyoxypropylene block polymer (Lutrol F68 manufactured by BASF Co., and the like). These hydrophilic polymers may be used alone or as a mixture of two or more and mixed preferably in an amount of from 0.2 to 3% by weight, more preferably, from 0.5 to 2% by weight in view of the viscosity and stickiness of the cream.

Examples of the oily substance include fatty acid esters such as diisopropyl adipate, diisopropyl sebacate, diethyl sebacate, middle-length fatty acid triglycerides, middle-length fatty acid propylene glycols, isopropyl myristate, and the like; fatty acids such as stearic acid, oleic acid, myristic acid, and the like; higher alcohols such as cetanol, stearyl alcohol, cetostearyl alcohol, oleyl alcohol, behenyl alcohol, and the like; hydrocarbons such as white petrolatum, liquid paraffin, squalane, and the like; plant oils and fats such as olive oil, hohoba oil, castor oil, and the like; and other oily substances such as crotamiton, benzyl alcohol, and the like. In the case of the cream preparation, the oily substance is mixed in an amount of from 2 to 20% by weight, preferably from 5 to 15% by weight, in view of the spreadability of cream, transdermal absorption, stickiness, shining, and instability in production of preparations (e.g., liquid separation), and the like. In the case of the ointment preparation, it is mixed in an amount of from 2 to 20% by weight, preferably from 3 to 7% by weight.

Examples of the surface active agent include sorbitan fatty acid esters such as sorbitan monostearate, sorbitan sesquistearate, and the like; glycerol fatty acid esters such as glyceryl monostearate, diglyceryl monooleate, and the like; polyoxyethylenesorbitan fatty acid esters such as polyoxyethylene(20)sorbitan monostearate, polyoxyethylene(20)sorbitan monooleate, and the like; polyethylene glycol fatty acid esters such as polyoxyethylene(10) monostearate, polyoxyethylene(10) monolaurate, and the like; polyoxyethylene alkyl ethers such as polyoxyethylene(9) lauryl ether, polyoxyethylene(23) cetyl ether, and the like; polyoxyethylene alkylphenyl ethers such as polyoxyethylene(10) nonylphenyl ether, polyoxyethylene(10) octylphenyl ether, and the like; and polyoxyethylene hydrogenated castor oil such as polyoxyethylene(10) hydrogenated castor oil, polyoxyethylene(60) hydrogenated castor oil, and the like. These surface active agents may be used alone or as a mixture of two or more and mixed in an amount of from 0.5 to 7% by weight, preferably, from 1 to 5% by weight.

Examples of the basic substance include inorganic or organic bases such as potassium hydroxide, sodium hydroxide, triethanolamine, diisopropanolamine, monoethanolamine, and the like, and organic bases are preferable from the viewpoint of the transdermal absorption. These basic substance may be mixed in an amount of from 0.01 to 5% by weight, preferably from 0.1 to 2% by weight.

In addition, in order to enhance the transdermal absorption of nimesulide, the absorption enhancer may be mixed in the above-described pharmaceutical preparation depending on the type of the pharmaceutical prescription. Examples of the absorption enhancer include organic bases, crotamiton, middle-length fatty acid esters, 1-menthol, benzyl alcohol, and the like. The organic base facilitates the release of nimesulide from the base since it makes nimesulide water-soluble by forming a salt with nimesulide. Examples of the organic base include diisopropanolamine, meglumine, triethanolamine, and 1-(2-hydroxyethyl)pyrrolidine, and diisopropanolamine and 1- (2-hydroxyethyl)pyrrolidine are the most preferable. The absorption enhancer is mixed in an amount of from 0.1 to 20% by weight, preferably from 0.2 to 10% by weight, alone or as a mixture of two or more.

The above-described basic substance and the organic base as an absorption enhancer act also as a pH controlling agent of the preparation. That is, when pH of the pharmaceutical preparation is too low (e.g., 3 or less), the high acidity makes skin irritation strong. When pH is too high (e.g., 9 or more), the transdermal absorbability of the medical agent is reduced, skin irritation becomes strong, and the pharmaceutical preparation colors yellow. Accordingly, the pH of the pharmaceutical preparation is controlled preferably in the range of from 4 to 8 by the amount of the above-described basic substance or the absorption enhancer to be mixed.

In addition to the above-described components, animal oils and fats, waxes, hydrocarbons, antiseptics, wetting agents, and the like may be added and mixed. Examples of the animal oil and fat include beef tallow, pork tallow, horse oil, and the like. Examples of the wax include microcrystalline wax, montan wax, bees wax, and the like. Examples of the hydrocarbon include paraffin, ceresine, and the like. Examples of the antiseptic include methylparaben, propylparaben, butylparaben, and the like. Examples of the wetting agent include polyhydric alcohols such as glycerol, 1,3-butylene glycol, propylene glycol, dipropylene glycol, and the like. These additives may be the mixed in amounts generally employed for cream and ointment preparations.

EXAMPLES

The present invention is illustrated in greater detail with reference to the following Examples.

Example 1

| Component | % by weight |
| --- | --- |
| (1) Nimesulide (Particle Diameter: 5 to 20 $\mu$m) | 3 |
| (2) Carboxyvinyl Polymer | 1 |
| (3) Diisopropyl Sebacate | 5 |
| (4) Isopropyl Myristate | 10 |
| (5) Crotamiton | 3 |
| (6) Polyoxyethylene (20) sorbitan Monostearate | 5 |

-continued

| Component | % by weight |
|---|---|
| (7) Methylparaben | 0.1 |
| (8) Propylparaben | 0.1 |
| (9) Diisopropanolamine | 0.5 |
| (10) Purified Water | 72.3 |
| | 100.0 |

The components (3), (4), (5), (6), and (8) were melted by heating at 75° C. A solution which had been separately prepared by dissolving the component (7) in about 90% of the component (10) at 75° C. was added, and the mixture was stirred to effect emulsification. The component (2) was gradually added at 50° C. and the mixture was thoroughly stirred. Then, the component (1) was gradually added and dispersed by stirring. Then, a solution which had been prepared by dissolving the component (9) in the remaining component (10) was added, and the mixture was stirred until the mixture became homogenous to obtain an antiinflammatory cream preparation containing nimesulide.

Example 2

| Component | % by weight |
|---|---|
| (1) Nimesulide (Particle Diameter: 20 to 40 μm) | 3 |
| (2) Carboxyvinyl Polymer | 1 |
| (3) Diisopropyl Sebacate | 5 |
| (4) Isopropyl Myristate | 10 |
| (5) Crotamiton | 3 |
| (6) Polyoxyethylene (20) sorbitan Monostearate | 5 |
| (7) Methylparaben | 0.1 |
| (8) Propylparaben | 0.1 |
| (9) Diisopropanolamine | 0.5 |
| (10) Purified Water | 72.3 |
| | 100.0 |

The components (3), (4), (5), (6), and (8) were melted by heating at 75° C. A solution which had been separately prepared by dissolving the component (7) in about 90% of the component (10) at 75° C. was added, and the mixture was stirred to effect emulsification. The component (2) was gradually added at 50° C. and the mixture was thoroughly stirred. Then, the component (1) was gradually added and dispersed by stirring. Then, a solution which had been prepared by dissolving the component (9) in the remaining component (10) was added, and the mixture was stirred until the mixture became homogenous to obtain an antiinflammatory cream preparation containing nimesulide.

Example 3

| Component | % by weight |
|---|---|
| (1) Nimesulide (Particle Diameter: 5 to 20 μm) | 3 |
| (2) Carboxyvinyl Polymer | 1 |
| (3) Diethyl Sebacate | 5 |
| (4) Middle-length Fatty Acid Triglyceride | 8 |
| (5) Crotamiton | 3 |
| (6) Polyoxyethylene (20) sorbitan Monostearate | 5 |
| (7) Methylparaben | 0.1 |
| (8) Propylparaben | 0.1 |
| (9) 1-(2-Hydroxyethyl)pyrrolidine | 0.5 |
| (10) Purified Water | 74.3 |
| | 100.0 |

The components (3), (4), (5), (6), and (8) were melted by heating at 75° C. A solution which had been separately prepared by dissolving the component (7) in about 90% of the component (10) at 75° C. was added, and the mixture was stirred to effect emulsification. The component (2) was gradually added at 50° C. and the mixture was thoroughly stirred. Then, the component (1) was gradually added and dispersed by stirring. Then, a solution which had been prepared by dissolving the component (9) in the remaining component (10) was added, and the mixture was stirred until the mixture became homogenous to obtain an antiinflammatory cream preparation containing nimesulide.

Example 4

| Component | % by weight |
|---|---|
| (1) Nimesulide (Particle Diameter: 5 to 20 μm) | 5 |
| (2) Carboxyvinyl Polymer | 1 |
| (3) Diethyl Sebacate | 5 |
| (4) Middle-length Fatty Acid Triglyceride | 8 |
| (5) Crotamiton | 3 |
| (6) Polyoxyethylene (20) sorbitan Monostearate | 5 |
| (7) Methylparaben | 0.1 |
| (8) Propylparaben | 0.1 |
| (9) 1-(2-Hydroxyethyl)pyrrolidine | 0.5 |
| (10) Purified Water | 72.3 |
| | 100.0 |

The components (3), (4), (5), (6), and (8) were melted by heating at 75° C. A solution which had been separately prepared by dissolving the component (7) in about 90% of the component (10) at 75° C. was added, and the mixture was stirred to effect emulsification. The component (2) was gradually added at 50° C. and the mixture was thoroughly stirred. Then, the component (1) was gradually added and dispersed by stirring. Then, a solution which had been prepared by dissolving the component (9) in the remaining component (10) was added, and the mixture was stirred until the mixture became homogenous to obtain an antiinflammatory cream preparation containing nimesulide.

Example 5

| Component | % by weight |
|---|---|
| (1) Nimesulide (Particle Diameter: 0.5 to 10 μm) | 3 |
| (2) Carboxyyinyl Polymer | 1 |
| (3) Diisopropyi Adipate | 5 |
| (4) Isopropyl Myristate | 10 |
| (5) 1-Menthol | 2 |
| (6) Polyoxyethylene (20) sorbitan Monostearate | 5 |
| (7) Methylparaben | 0.1 |
| (8) Propylparaben | 0.1 |
| (9) Diisopropanolamine | 0.5 |
| (10) Purified Water | 73.3 |
| | 100.0 |

The components (3), (4), (5), (6), and (8) were melted by heating at 75° C. A solution which had been separately prepared by dissolving the component (7) in about 90% of the component (10) at 75° C. was added, and the mixture was stirred to effect emulsification. The component (2) was gradually added at 50° C. and the mixture was thoroughly stirred. Then, the component (1) was gradually added and dispersed by stirring. Then, a solution which had been prepared by dissolving the component (9) in the remaining component (10) was added, and the mixture was stirred until the mixture became homogenous to obtain an antiinflammatory cream preparation containing nimesulide.

Example 6

| Component | % by weight |
| --- | --- |
| (1) Nimesulide (Particle Diameter: 0.5 to 10 μm) | 0.5 |
| (2) Stearic Acid | 5 |
| (3) Diisopropyl Adipate | 3 |
| (4) Cetanol | 5 |
| (5) Middle-length Fatty Acid Triglyceride | 7 |
| (6) Polyoxyethylene (23) Cetyl Ether | 3 |
| (7) Sorbitan Monostearate | 1 |
| (8) 1,3-Butylene Glycol | 5 |
| (9) Diisopropanolamine | 1 |
| (10) Sodium Benzoate | 0.1 |
| (11) Purified Water | 69.4 |
| | 100.0 |

The components (2), (3), (4), (5), (6), and (7) were melted by heating at 75° C. A solution which had been separately prepared by dissolving the components (8), (9), and (10) in the component (11) at 75° C. was added, and the mixture was stirred to effect emulsification. The component (1) was gradually added at 50° C. or lower, and the mixture was stirred until the mixture became homogenous to obtain an antiinflammatory cream preparation containing nimesulide.

Example 7

| Component | % by weight |
| --- | --- |
| (1) Nimesulide (Particle Diameter: 0.5 to 10 μm) | 3 |
| (2) Crotamiton | 3 |
| (3) Diethyl Sebacate | 5 |
| (4) Microcrystalline Wax | 10 |
| (5) Middle-length Fatty Acid Triglyceride | 7 |
| (6) Propylene Glycol Fatty Acid Ester | 10 |
| (7) Behenyl Alcohol | 4 |
| (8) Diisopropanolamine | 0.2 |
| (9) Dipropylene glycol | 7 |
| (10) Propylene Glycol Monostearate | 7 |
| (11) White Petrolatum | 43.8 |
| | 100.0 |

The components (2), (3), (4), (5), (6), (7), (8), (9), (10), and (11) were melted by heating at 80° C. The component (1) was gradually added at 50° C. and dispersed by stirring to obtain an antiinflammatory ointment preparation containing nimesulide.

Example 8

(A dispersed-type cream preparation in which the active ingredient has the particle diameter of 76 to 180 μm)

| Component | % by weight |
| --- | --- |
| (1) Nimesulide (Particle Diameter: 75 to 180 μm) | 3 |
| (2) Carboxyvinyl Polymer | 1 |
| (3) Isopropyl Myristate | 15 |
| (4) Polyoxyethylene (20) sorbitan Monostearate | 5 |
| (5) Methylparaben | 0.1 |
| (6) Propylparaben | 0.1 |
| (7) Propylene Glycol | 3 |
| (8) Diethanolamine | 0.5 |
| (9) Purified Water | 72.3 |
| | 100.0 |

The components (3), (4), and (6) were melted by heating at 75° C. A solution which had been separately prepared by dissolving the component (6) and (7) in about 90% of the component (9) at 75° C. was added, and the mixture was stirred to effect emulsification. The component (2) was gradually added at 50° C. and the mixture was thoroughly stirred. Then, the component (1) was gradually added and dispersed by stirring. Then, a solution which had been prepared by dissolving the component (8) in the remaining component (9) was added, and the mixture was stirred until the mixture became homogenous to obtain an antiinflammatory cream preparation containing nimesulide.

Reference Example (A cream preparation in which the active ingredient is dissolved)

| Component | % by weight |
| --- | --- |
| (1) Nimesulide | 3 |
| (2) Carboxyvinyl Polymer | 1 |
| (3) Isopropyl Myristate | 15 |
| (4) Polyoxyethylene (20) sorbitan Monostearate | 5 |
| (5) Methylparaben | 0.1 |
| (6) Propylparaben | 0.1 |
| (7) 1,3-Butylene Glycol | 3 |
| (8) Diethanolamine | 6 |
| (9) Purified Water | 66.8 |
| | 100.0 |

The components (3), (4), and (6) were melted by heating at 75° C. A solution which had been separately prepared by dissolving the components (5) and (7) in about 90% of the component (9) at 75° C. was added, and the mixture was stirred to effect emulsification. The component (2) was gradually added at 50° C. and the mixture was thoroughly stirred to dissolve the component (2). Then, the component (1) was gradually added and mixed by stirring. Then, a solution which had been prepared by dissolving the component (8) in the remaining component (9) was added, and the mixture was stirred until the mixture became homogenous to obtain an antiinflammatory cream preparation containing nimesulide.

Test Example 1

Suppression test of carrageenin-induced rat foot edema

The antiinflammatory activity of the cream preparations of Examples 1, 2, 5, 7, and 8 and Reference Example as well as a commercially available indomethacin-containing cream preparation were examined based on the suppression of carrageenin-induced rat foot edema.

Test Method

The test substance was applied on a right foot sole of male Wister rats each weighing 132 to 150 g, and the right foot sole was fixed by covering with wrapping film. When the drug was applied, the animal was shackled with a plastic neck shackle and put into an individual cage in order to avoid oral ingestion of the drug. After 4 hours from the application of the drug, the drug was completely removed with absorbent cotton containing slightly warm water. Immediately, a physiological saline containing 1% carrageenin (0.1 ml) was subcutaneously injected at foot sole. After 3 hours, the foot volume was measured, and the edematization ratio was calculated based on the foot volume before injection of prophlogistic substance. The test results are shown in Table 1.

TABLE 1

| Sample (administered amount: 100 mg/site) | Number of animals | Edematization ratio (%) (after 3 hours) |
| --- | --- | --- |
| Control | 8 | 77.6 |
| Cream preparation of Example 1 | 8 | 38.9 |
| Cream preparation of Example 2 | 8 | 35.1 |
| Cream preparation of Example 5 | 8 | 45.6 |
| Cream preparation of Example 7 | 8 | 50.6 |
| Cream preparation of Example 8 | 8 | 64.6 |
| Cream preparation of Reference Example | 8 | 53.1 |
| Commercially available indomethacin cream preparation | 8 | 68.6 |

From the results in Table 1, it is clear that the pharmaceutical preparations of Examples 1, 2, 5, 7, and 8 showed superior antiinflammatory effect in comparison with the commercially available indomethacin cream preparation, which is equal or higher even in comparison with the cream preparation of Reference Example containing nimesulide in a dissolved state.

Test Example 2

Coloring test

The cream preparations of the present invention and the cream preparation of the Reference Example were prepared and spread on a cotton cloth, and the degree of coloring was observed. The test results are shown in Table 2.

TABLE 2

| Sample | Appearance at the time of preparation | Coloring of cloth |
| --- | --- | --- |
| Cream preparation of Example 1 | Slightly yellowish white cream | Almost no coloring |
| Cream preparation of Example 2 | Slightly yellowish white cream | Almost no coloring |
| Cream preparation of Reference Example | Yellow cream | Colored yellow |

As is clear from Table 2, the cloth was colored in the case of the cream preparation of Reference Example containing nimesulide in a dissolved state but the cream preparations of Examples 1 and 2 according to the present invention showed almost no coloring.

Effect of the Invention

The antiinflammatory agent for external use of the present invention in which nimesulide is mixed in a dispersed state has pharmacological effects equal to or higher than those of the dissolved-type preparation, has no skin irritation, is safe, and does not soil the skin and clothes since it is not colored. Accordingly, the present invention is extremely useful as an agent in the field of dermatology for treating eczema, dermatitis, and the like, and as an antiinflammatory external preparation in the field of orthosis for treating chronic articular rheumatism, osteoarthritis, shoulder joint periarthritis, peritendinitis, myalgia, and tumentia and pain after injury.

We claim:

1. An antiinflammatory cream preparation for external use comprising nimesulide in a dispersed phase having a mean particle diameter of from 0.01 to 75 μm in an amount of from 0.1 to 5% by weight mixed in a gel-like cream base comprising a carboxyvinyl polymer in an amount of from 0.2 to 3% by weight, an oily substance comprising diisopropyl sebacate and isopropyl myristate in an amount of from 2 to 20% by weight, a nonionic surface active agent in an amount of from 0.5 to 7% by weight, a basic substance in an amount of from 0.01 to 5% by weight, and water in an amount of from 50 to 90% by weight.

2. The antiinflammatory agent for external use as recited in claim 1, which has a pH of from 4 to 8.

3. The antiinflammatory agent for external use as recited in claim 1, further comprising an absorption enhancer which is an organic base, crotamiton, a middle-length fatty acid ester, 1-menthol, and/or benzyl alcohol.

4. The antiinflammatory agent for external use as recited in claim 3, wherein said organic base is diisopropanolamine, meglumine, triethanolamine, and/or 1-(2-hydroxyethyl) pyrrolidine.

5. An antiinflammatory ointment preparation for external use comprising nimesulide in a dispersed phase having a mean particle diameter of from 0.01 to 75 μm in an amount of from 0.1 to 5% by weight mixed in a petrolatum ointment base component comprising a white petrolatum in an amount of from 35 to 80% by weight, an oily substance comprising diisopropyl sebacate and isopropyl myristate in an amount of from 2 to 20% by weight, and a nonionic surface active agent in an amount of from 0.5 to 7% by weight.

6. A process for producing an anti-inflammatory agent for external use, which comprises:

gradually adding from 0.1 to 5% by weight of nimesulide as an active ingredient in a form of fine particles into a base component, and dispersing nimesulide by stirring, said particles having a mean particle diameter of from 0.01 to 75 μm, and said base component comprising a carboxyvinyl polymer in an amount of from 0.2 to 3% by weight, an oily substance comprising diisopropyl sebacate and isopropyl myristate in an amount of from 2 to 20% by weight, a nonionic surface active agent in an amount of from 0.5 to 7% by weight, water in an amount of from 50 to 90% by weight, and from 0.01 to 5% by weight of a basic substance.

7. The process as recited in claim 6, wherein an oil component melted by heating is used as the base component.

8. The process as recited in claim 6, wherein an oil phase of heat-melted oil components and an aqueous phase in which water-soluble components have been dissolved are mixed by stirring, and used as the base component.

* * * * *